United States Patent
Klein et al.

(10) Patent No.: US 7,030,247 B2
(45) Date of Patent: Apr. 18, 2006

(54) METHOD FOR THE PRODUCTION OF BIPERIDIN

(75) Inventors: Peter Klein, Birkenheide (DE); Marco Thyes, Ludwigshafen (DE); Markus Grosse, Schwetzingen (DE); Klaus Martin Weber, Ludwigshafen (DE)

(73) Assignee: Abbott GmbH & Co. DG, Wiesbaden (DE)

( * ) Notice: Subject to any disclaimer, the term of this patent is extended or adjusted under 35 U.S.C. 154(b) by 3 days.

(21) Appl. No.: 10/477,761

(22) PCT Filed: May 17, 2002

(86) PCT No.: PCT/EP02/05496

§ 371 (c)(1),
(2), (4) Date: Mar. 29, 2004

(87) PCT Pub. No.: WO02/094800

PCT Pub. Date: Nov. 28, 2002

(65) Prior Publication Data

US 2004/0147753 A1    Jul. 29, 2004

(30) Foreign Application Priority Data

May 18, 2001   (DE) ................................ 101 24 451

(51) Int. Cl.
*C07D 211/06* (2006.01)
(52) U.S. Cl. .................................................. 546/205
(58) Field of Classification Search ................. 546/205
See application file for complete search history.

(56) References Cited

U.S. PATENT DOCUMENTS

| 2,789,110 A | 4/1957 | Klavehn |
| 6,835,839 B1 * | 12/2004 | Klein et al. ................. 546/205 |

FOREIGN PATENT DOCUMENTS

| DE | 1 005 067 | 3/1957 |
| JP | 11189729 A | 7/1999 |
| WO | WO 02/094800 | 5/2002 |

OTHER PUBLICATIONS

Ronald Breslow and Uday Maitra, On the Origin of Product Selectivity in Aqueous Dies-Alder Reactions, Tetrahedron Letters. vol. 25. No. 12, pp 1239-1240, 1984, Great Britain.
Ullmans Enzykopadie der technischen Chemie, 4th Edition, vol. 21, Verlag Chemie, 1982, p. 627.
J. G. Dinwiddie and S. P. McManus (J. Org. Chem., 1965, 30, 766).

* cited by examiner

*Primary Examiner*—Rita Desai
(74) *Attorney, Agent, or Firm*—Wood, Phillips, Katz, Clark & Mortimer

(57) ABSTRACT

The invention relates to a method for the production of biperiden by reacting an exo/endo mixture of 1-(bi-cyclo[2.2.1]hept-5-en-2-yl)-3-piperidino-1-propanone with a phenyl magnesium compound to form an isomer mixture of 1-(bi-cyclo[2.2.1]hept-5-en-2-yl)-1-phenyl-3-piperidino-1-propanol, whereby biperiden is obtained therefrom by conversion of said mixture into corresponding hydrochloride, isolation of said hydrochloride, reconversion to the free base and crystallization of said biperiden.

11 Claims, No Drawings

METHOD FOR THE PRODUCTION OF BIPERIDIN

CROSS-REFERENCE TO RELATED APPLICATION

This application is a Section 371 National Stage Application of Application No. PCT/EP02/05496 filed on May 17, 2002.

The present invention relates to a method for the production of biperiden.

Biperiden is a well-known central anticholinergic agent and is employed for the treatment of Parkinson's disease (Ullmanns Enzyklopädie der technischen Chemie, 4th edition, volume 21, Verlag Chemie, 1982, p. 627). It comprises a racemate of 1-(bicyclo[2.2.1]hept-5-en-2-yl(exo,R))-1-phenyl-3-piperidino-propanol(1,S) and 1-(bicyclo[2.2.1]hept-5-en-2-yl(exo,S))-1-phenyl-3-piperidinopropanol(1,R) (Ia) and represents one of four possible pairs of enantiomers (Ia-d) of the amino alcohol 1-(bicyclo[2.2.1]hept-5-en-2-yl)-1-phenyl-3-piperidino-1-propanol (I).

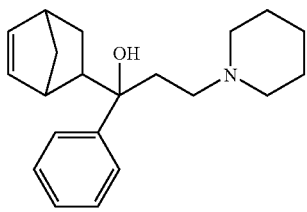

(I)

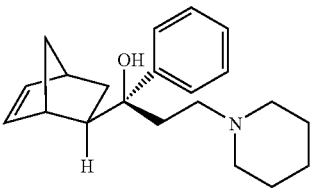

(Ia)

(exo, R)/(1,S)

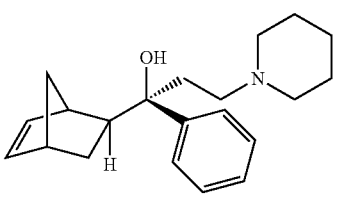

(exo, S)/(1,R)

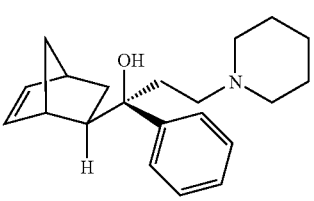

(Ib)

(exo, R)/(1,R)

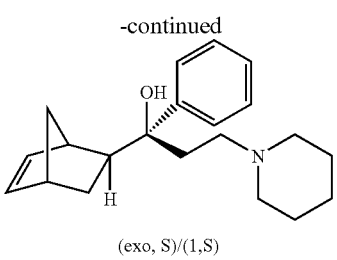

(exo, S)/(1,S)

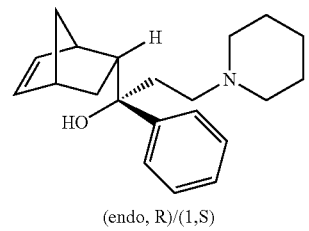

(Ic)

(endo, R)/(1,S)

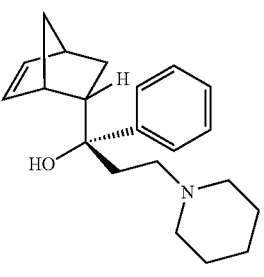

(endo, S)/(1,R)

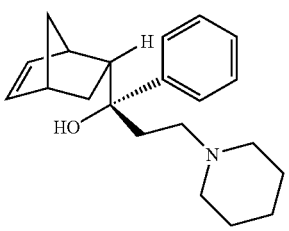

(Id)

(endo, R)/(1,R)

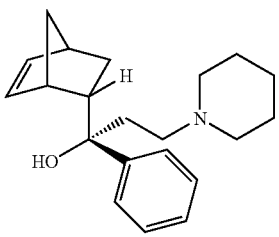

(endo, S)/(1,S)

DE 1 005 067 and U.S. Pat. No. 2,789,110 describe the preparation of the amino alcohol I by reacting 1-(bicyclo[2.2.1]hept-5-en-2-yl)-3-piperidino-1-propanone (II) with a phenylmagnesium halide. U.S. Pat. No. 2,789,110 additionally describes the preparation of the propanone II starting from 1-(bicyclo[2.2.1]hept-5-en-2-yl)-ethanone (III), paraformaldehyde and piperidine hydrochloride in a Mannich reaction, and the preparation of the ethanone III from cyclopentadiene and methyl vinyl ketone in a Diels-Alder cycloaddition.

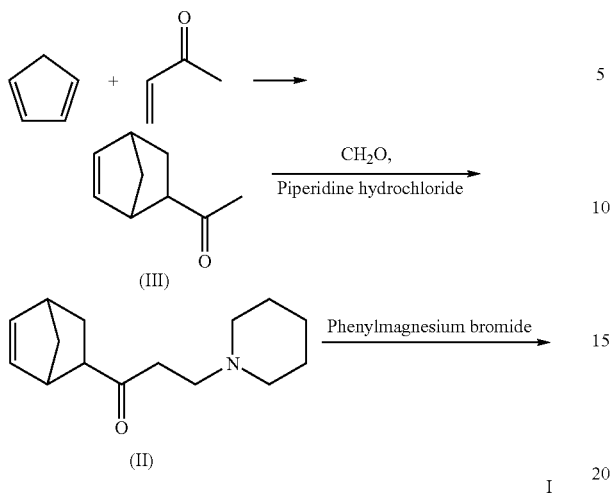

Neither DE 1 005 067 nor U.S. Pat. No. 2,789,110 disclose whether the amino alcohol I obtained in this way is a mixture of isomers or a pure isomer.

The precursor for preparing the propanol, 1-(bicyclo[2.2.1]hept-5-en-2-yl)-3-piperidino-1-propanone (II), can exist in two isomeric forms, as exo or as endo isomer (II-exo, II-endo), and only the exo form is able to afford biperiden in the abovementioned reaction with a phenylmagnesium halide.

The structural formulae of II-exo and of II-endo show for the sake of simplicity in each case only one of two possible enantiomers of the exo isomer and endo isomer, respectively. However, the designation II-exo or II-endo relates hereinafter to the pair of enantiomers of the exo or endo form.

1-(Bicyclo[2.2.1]hept-5-en-2-yl)ethanone (III), the starting substance for synthesizing the propanone II, may also exist both as exo and as endo isomer (III-exo, III-endo) and, correspondingly, only reaction of the exo isomer leads in the subsequent steps to biperiden.

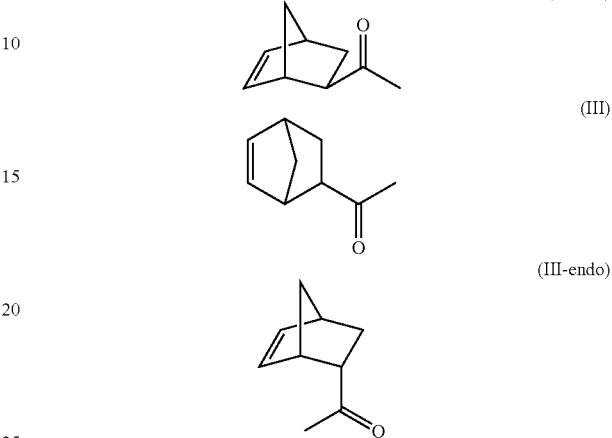

The structural formulae of III-exo and of III-endo show for the sake of simplicity in each case only one of two possible enantiomers of the exo isomer and endo isomer, respectively. However, the designation III-exo or III-endo relates hereinafter to the pair of enantiomers of the exo or endo form.

It is not possible to infer any information about the configuration of the precursors III and intermediates II employed in any of the abovementioned publications.

It is known that 1-(bicyclo[2.2.1]hept-5-en-2-yl)ethanone (III) is obtained from the cycloaddition in an exo/endo ratio of 1:4 (e.g. R. Breslow, U. Maitra, Tetrahedron Letters, 1984, 25, 1239). Since the prior art mentioned at the outset makes no statements at all about the stereochemistry of the ethanone III, it must be assumed that the ethanone III was employed in this ratio of isomers to prepare the amino alcohol I.

The preparation of exo-1-(bicyclo[2.2.1]hept-5-en-2-yl)ethanone (III-exo) was described in 1965 by J. G. Dinwiddie and S. P. McManus (J. Org. Chem., 1965, 30, 766). This entails exo/endo mixtures of 1-(bicyclo[2.2.1]hept-5-en-2-yl)ethanone (III) in which the endo content predominates being heated in methanol in the presence of sodium methanolate and isomerizing to mixtures with an exo content of about 70%. It is possible to obtain from this by fractional distillation and, where appropriate, redistillation of the distillate exo-1-(bicyclo[2.2.1]hept-5-en-2-yl)ethanone (III-exo) with a purity of up to 95%.

Experiments by the applicant have shown that even on use of virtually pure exo-1-(bicyclo[2.2.1]hept-5-en-2-yl)ethanone (III-exo), i.e. of an ethanone III with an exo content of at least 95%, as starting material it is possible to obtain pure biperiden (Ia) in only low yields, with both the reaction of 1-(bicyclo[2.2.1]hept-5-en-2-yl)-3-piperidino-1-propanone (II) with a phenylmagnesium halide and the isolation of biperiden (Ia) from the mixture of isomers of the amino alcohol I formed in this reaction proceeding with a poor yield of biperiden (Ia). Pure biperiden means a biperiden (Ia) with a purity of at least 99.0%, as is generally necessary for pharmaceutical applications.

It is an object of the present invention to provide a method for producing biperiden (Ia) which affords the latter in a higher yield.

It has been possible to achieve this object by a method for producing biperiden by reacting 1-(bicyclo[2.2.1]hept-5-en-2-yl)-3-piperidino-1-propanone (II) with an exo/endo ratio of at least 2.5:1 with a phenylmagnesium compound to give a biperiden (Ia)-containing mixture of isomers of 1-(bicyclo-[2.2.1]hept-5-en-2-yl)-1-phenyl-3-piperidino-1-propanol (I), characterized in that the isolation of biperiden (Ia) from the mixture of isomers comprises the following steps:

a) reaction of the mixture of isomers with hydrogen chloride in a mixture of water and a polar organic solvent of limited or infinite miscibility with water, and isolation of the hydrochloride formed thereby,
b) reaction of the hydrochloride in a mixture of water and at least one polar dialkyl ether of limited or zero miscibility with water and having 4 to 8 C atoms with a base,
c) separation of the two phases formed at elevated temperature,
d) evaporation of part of the ether from the organic phase and
e) crystallization of the biperiden by cooling.

The exo and endo isomers employed in the method of the invention comprise, as already described for the exo and endo ethanone III-exo and III-endo and for the exo and endo propanone II-exo and II-endo, pairs of enantiomers. In order to obtain biperiden (Ia), which is itself a racemate, racemic mixtures of enantiomers of the starting materials and of the intermediates are employed. However, the method of the invention can also be applied to pure enantiomers and to non-racemic mixtures of enantiomers.

Reaction of the propanone II with a suitable phenylmagnesium compound usually takes place in a suitable solvent. Suitable phenylmagnesium compounds are phenylmagnesium halides, for example phenylmagnesium chloride or phenylmagnesium bromide, diphenylmagnesium and phenylmagnesium alkoxides of the general formula IV

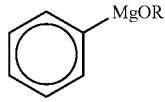

(IV)

in which R is $C_1$–$C_4$-alkyl such as methyl, ethyl, n-propyl, isopropyl or n-butyl, $C_4$–$C_6$-cycloalkyl such as cyclohexyl, $C_4$–$C_6$-cycloalkyl-$C_1$–$C_4$-alkyl such as 2-cyclohexylethyl, phenyl-$C_1$–$C_4$-alkyl such as benzyl, 2-phenylethyl or 3-phenylpropyl, substituted phenyl-$C_1$–$C_4$-alkyl such as 3,4-(methylenedioxy)benzyl, heteroaryl such as 8-quinolyl, heteroaryl-$C_1$–$C_4$-alkyl such as furfuryl, 2-thienylmethyl or 2-(2-thienyl)ethyl, or benzhydryl. Diphenylmagnesium and, in particular, the phenylmagnesium alkoxide is preferably used.

Suitable solvents for the reaction of II with the phenylmagnesium compound are aromatic compounds such as benzene, toluene, or xylenes, acyclic or cyclic ethers having 4 to 6 C atoms, mixtures thereof or mixtures of them with aliphatic or alicyclic hydrocarbons such as n-hexane or cyclohexane. Examples of suitable acyclic ethers are diethyl ether and tert-butyl methyl ether, and examples of suitable cyclic ethers are tetrahydrofuran and dioxane. Diethyl ether, tetrahydrofuran or dioxane or mixtures thereof are preferably used. The solvents are usually employed anhydrous, as normal for Grignard reactions.

The phenylmagnesium alkoxide IV is prepared in a generally known manner, e.g. by reacting diphenylmagnesium with an alcohol of the general formula ROH in which R is as defined above. Diphenyl-magnesium and the alcohol are for this purpose reacted in a molar ratio in the range from 1:0.9 to 1:1.5, preferably in the range from 1:1 to 1:1.2 and particularly preferably approximately equimolar. Diphenylmagnesium, which is usually generated in situ as described hereinafter, is ordinarily introduced into one of the abovementioned solvents suitable for Grignard reactions, and the alcohol is normally added in portions over a period of from 5 minutes up to about one hour at a temperature of from 0 to 80° C., preferably from 0 to 50° C. and particularly preferably from 0 to 40° C. After the addition is complete, the mixture can be left, or preferably stirred, in the same temperature range for 15 minutes to 2 hours, preferably 15 minutes to one hour, until the reaction is complete.

The diphenylmagnesium employed in the method of the invention is produced in a manner known per se. For example, dioxane can be added to a phenylmagnesium halide, e.g. phenylmagnesium chloride, in a suitable solvent, thus shifting the Schlenk equilibrium to result in diphenylmagnesium and the corresponding magnesium halide-dioxane complex. The latter usually precipitates, but is preferably not removed from the solution. Suitable solvents are generally acyclic and cyclic ethers preferably having 4 to 6 C atoms or mixtures thereof with aliphatic, alicyclic or aromatic hydrocarbons. Examples of suitable acyclic ethers are diethyl ether and tert-butyl methyl ether, and a suitable cyclic ether is tetrahydrofuran. The suitable aliphatic and alicyclic hydrocarbons include in particular n-hexane and cyclohexane, and examples of suitable aromatic hydrocarbons are benzene, toluene and xylenes.

Dioxane is ordinarily employed at least equimolar in relation to the phenylmagnesium halide. If diphenylmagnesium is to be used as phenylmagnesium compound, then dioxane is preferably employed in excess, for example in an excess of from 50 to 500 mol %, in particular from 100 to 300 mol % and specifically of from 100 to 200 mol %. If diphenylmagnesium is first to be converted into the phenylmagnesium alkoxide, preferably dioxane and the phenylmagnesium halide are employed in a molar ratio in the range from 1:1 to 1.5:1, in particular 1:1 to 1.2:1 and particularly preferably approximately equimolar.

The dioxane is added to the solution of the phenylmagnesium halide usually at a temperature in the range from −20 to 60° C., preferably in the range from −10 to 40° C.

The mixture obtained after addition of the dioxane is normally left for from 15 minutes to 2 hours, preferably 20 minutes to one hour, in the temperature range mentioned for the addition of the dioxane, before it is employed in the method of the invention.

Both the preparation of diphenylmagnesium, the reaction to give the phenylmagnesium alkoxide and the Grignard reaction of the phenylmagnesium compound with the propanone II are suitably carried out under an inert gas atmosphere. Examples of suitable inert gases are nitrogen and the noble gases such as argon, and mixtures thereof.

In the Grignard reaction of the propanone II with the phenyl-magnesium compound, ordinarily the phenylmagnesium compound and the propanol II are employed in a molar ratio in the range from 0.8:1 to 3:1, preferably from 1:1 to 3:1. Where diphenylmagnesium or the phenylmagnesium alkoxide is used, the phenylmagnesium compound and the propanone II are particularly preferably employed in a molar ratio in the range from 1:1 to 2:1, in particular from 1:1 to 1.3:1.

Ordinarily, the propanone II is added to the phenylmagnesium compound in the form of a solution in one of the abovementioned organic solvents suitable for Grignard reactions at a temperature in the range from −20° C. to the boiling point, preferably in the range from −10° to 90° C. and particularly preferably in the range from 0° C. to 70° C. The phenylmagnesium compound is moreover ordinarily employed in a concentration in the range from 0.1 to 10 mol/l, preferably in the range from 0.1 to 3 mol/l and particularly preferably in the range from 0.2 to 2 mol/l.

The propanone II can be added in one portion or, preferably, over a period of from a few minutes up to several hours, e.g. 5 minutes to 5 hours. The propanone II is added either in the form of a solution in one of the abovementioned inert solvents suitable for Grignard reactions or, preferably, in pure form. When added as solution, the concentration of the propanone II is ordinarily from 0.1 to 20 mol/l, preferably 1 to 15 mol/l. To complete the reaction, the reaction mixture is normally left at a temperature in the range from −20° C. to the boiling point of the reaction mixture, preferably in the range from −10° C. to 90° C. and particularly preferably in the range from 10° C. to 80° C. for from 15 minutes to 5 hours, specifically 30 minutes to 2 hours, during which it is preferably stirred to improve mixing. Workup is, as usual for Grignard reactions, by aqueous extraction, e.g. by quenching the reaction mixture with water, an aqueous ammonium chloride solution or an acidic aqueous solution, with the pH of the resulting mixture in the latter case subsequently being made alkaline, extracting the quenched mixture, where appropriate after removal of an organic phase, with a water-immiscible solvent suitable for dissolving the product, and removing the solvent from the extract or from the extract combined with the organic phase. Examples of suitable solvents are aromatic compounds such as benzene or toluene, the abovementioned acyclic ethers, esters such as ethyl acetate or chlorine-containing aliphatic compounds such as dichloromethane or trichloromethane.

The crude product obtained from the reaction of the propanone II with a phenylmagnesium compound consists essentially of the four diastereomeric pairs of enantiomers Ia to Id of the aminopropanol I, with the pair of enantiomers Ia (biperiden) forming the major quantity, usually at least 50%.

The biperiden (Ia) is isolated from the mixture of diastereomers by dissolving the latter with heating, preferably at a temperature of from 40 to 80° C., in particular from 50 to 70° C., in a mixture of water and a polar, water-miscible organic solvent. Suitable solvents are $C_1$–$C_3$-alkanols, i.e. methanol, ethanol, n-propanol and isopropanol. Aqueous isopropanol is preferably used, particularly preferably 70 to 95% isopropanol and especially 90% isopropanol. The percentage data given here and hereinafter in relation to the isopropanol content are based on the volume of the isopropanol relative to the total volume of the water-containing solvent. HCl is added to this solution, for example in the form of a solution of hydrogen chloride in an organic solvent, preferably in one of the $C_1$–$C_3$-alkanols mentioned, with preference in isopropanol, or in the form of hydrochloric acid. HCl is employed at least equimolar in relation to the amino alcohol I, preferably in an excess of from 5 to 50 mol % and particularly preferably from 5 to 20 mol %. The addition preferably takes place at elevated temperature, e.g. at 40 to 80° C. and in particular at 50 to 70° C. To complete the reaction after addition is complete, the reaction mixture is left at a temperature of from 50° C. up to the boiling point of the reaction mixture for 0.5 to 3 hours, preferably while stirring. In a preferred embodiment, the reaction mixture is stirred at 55 to 65° C. for the first two thirds of the time and then stirred at the reflux temperature for one third of the time. The reaction mixture is then cooled to a temperature in the range from 0 to 30° C., where appropriate stirred in this temperature range for up to several hours, e.g. up to 10 hours, preferably up to 5 hours, and then the hydrochloride which has formed is removed from the solution in a conventional way.

For further purification of the hydrochloride, it is generally taken up wet or dry in water and a sufficient amount of one or more polar dialkyl ethers of limited or zero miscibility with water and having 4 to 8 C atoms, such as diethyl ether, tert-butyl methyl ether and especially diisopropyl ether, and a suitable base is added to the mixture. Suitable amounts of organic solvents are, for example, from 4 to 10 ml of solvent per gram of dry hydrochloride. Water and organic solvent are preferably employed in a ratio in the range from 1:2 to 1:5 by volume.

Suitable bases are alkali metal and alkaline earth metal hydroxides, and alkali metal carbonates; sodium or potassium hydroxide or their aqueous solutions are particularly preferably used, sodium hydroxide or sodium hydroxide solution in particular are used. However, it is also possible to use water-soluble organic bases, for example amines having aliphatic substituents and 2 to 8 C atoms. The base is employed at least equimolar, preferably in excess, in particular in an excess of from 5 to 15 mol % based on the hydrochloride.

The reaction with the base takes place according to the invention at elevated temperature. For this purpose, before, during or, preferably, after addition of the base the mixture is heated to a temperature in the range of 25° C. up to the boiling point of the reaction mixture, preferably in the range from 30 to 70° C., and when diisopropyl ether is used as dialkyl ether preferably in the range from 40 to 65° C., in particular from 55 to 60° C. This generally results in two clear phases which are separated at elevated temperature, i.e. above 25° C., preferably 30–70° C., in the case where diisopropyl ether is used as dialkyl ether in the abovementioned temperature range. The organic phase is washed with water at elevated temperature, i.e. above 25° C., preferably 30–70° C., in the case where diisopropyl ether is used as dialkyl ether in the abovementioned temperature range, and then concentrated preferably under atmospheric pressure by removing the solvent until the weight/volume ratio of the product to the solvent is in the range from 1:2 to 1:6, preferably from 1:3 to 1:4.5. When the mixture is cooled to room temperature or below, but preferably not below −10° C., pure biperiden (Ia) crystallizes out and is isolated by conventional methods for isolating solids, e.g. filtering off the solid or decanting off the mother liquor.

The biperiden (Ia) obtainable by the purification of the invention is obtainable, especially on use of phenylmagnesium or the phenylmagnesium alkoxide, in a higher yield, in a higher purity and in fewer steps than by conventional methods. The purity is usually at least 99.0% or better.

Biperiden (Ia) can then be converted with a pharmacologically acceptable acid in a conventional manner into its acid addition salt. Examples of suitable acids are hydrohalic acids, in particular hydrogen chloride or hydrochloric acid, and organic mono- or dicarboxylic acids such as acetic acid, oxalic acid, maleic acid, fumaric acid, lactic acid, tartaric acid, adipic acid or benzoic acid, also phosphoric acid and sulfuric acid, and the acids mentioned in "Fortschritte der Arzneimittelforschung", volume 10, pages 224 et seq., Birkhäuser Verlag, Basle, Stuttgart, 1966. Biperiden (Ia) is normally marketed as hydrochloride.

The 1-(bicyclo[2.2.1]hept-5-en-2-yl)-3-piperidino-1-propanone (II) employed in the Grignard reaction is obtained by reacting exo-1-(bicyclo[2.2.1]hept-5-en-2-yl)ethanone (III-exo) in a Mannich reaction in the presence of an acid with piperidine and a formaldehyde source or with the adduct of piperidine and formaldehyde, preferably in a suitable solvent.

Hereinafter, exo-1-(bicyclo[2.2.1]hept-5-en-2-yl)ethanone (III-exo) is intended to mean an ethanone III which consists of at least 96%, preferably at least 97% and particularly preferably at least 98% of the exo isomer III-exo.

Suitable solvents are, in particular, $C_1$–$C_4$-alkanols, e.g. methanol, ethanol, n-propanol, isopropanol, sec-butanol and isobutanol. Isopropanol is preferably used. The exo ethanone (III-exo) and piperidine are usually employed in a molar ratio in the range from 0.5:1 to 1.5:1, preferably 1:1. Formaldehyde is normally present in excess, it being possible for the excess to be up to 100 mol % based on piperidine, in particular up to 50 mol %. Formaldehyde can in this connection be employed either gaseous, as formalin, as trioxane or as paraformaldehyde. It is preferred to use paraformaldehyde in particular in combination with piperidinium chloride. In a preferred procedure, the exo ethanone (III-exo), piperidine hydrochloride and paraformaldehyde are reacted together in molar ratios of 1:0.9–1.2:1–1.4. The solvent preferably used in this case is a $C_1$–$C_4$-alkanol, especially isopropanol. The reaction temperature is ordinarily in the range from 10° C. to the boiling point of the mixture. Heating to reflux is preferred.

The workup takes place in a manner known per se. For this purpose, usually first the solvent is removed under reduced pressure, and the residue is taken up in water. The aqueous solution obtained in this way is extracted with a suitable organic solvent, i.e. with a water-immiscible, moderately polar solvent, for example an aliphatic ether having 4 to 6 C atoms, such as diethyl ether, tert-butyl methyl ether or preferably diisopropyl ether. This extraction normally takes place at pH≦7 and serves to remove byproducts. In particular, the initially acidic solution is extracted and then the pH of the aqueous phase is raised by adding small amounts of base, and extraction is repeated, with a pH of≦7 being maintained. The aqueous phase is then preferably made alkaline by adding base in one or more stages, preferably to pH≧7.5, in particular pH 7.5 to 9 and specifically pH 8.0 to 8.5, in order to convert the 1-(bicyclo-[2.2.1]-hept-5-en-2-yl)-3-piperidino-1-propanone (II), which is still in the form of the acid addition salt, into the free amine. Bases suitable for this purpose are the usual inorganic bases such as KOH, NaOH, $Na_2CO_3$, $K_2CO_3$ and the like. The aqueous phase is then extracted one or more times with one of the abovementioned water-immiscible moderately polar solvents, preferably diisopropyl ether. To isolate the propanol II from the extract, the solvent is removed, where appropriate under reduced pressure. For further purification, the residue can be purified by a vacuum distillation under a pressure of preferably less than 10 mbar, particularly preferably less than 5 mbar and in particular less than 1 mbar. The resulting mixture consists of exo- and endo-1-(bicyclo-[2.2.1]hept-5-en-2-yl)-3-piperidino-1-propanone (II) in a ratio of at least 2.5:1, preferably of at least 3.0:1 and in particular of 3.5–4.0:1.

A preferred method for preparing the propanone II-exo, in particular the workup of the product obtained in the Mannich reaction of III-exo with piperidine and formaldehyde, is described in the parallel German patent application 10124449.5, the disclosure of which in this regard is incorporated herein by reference.

The exo-1-(bicyclo[2.2.1]hept-5-en-2-yl)ethanone (III-exo) used to prepare the 1-(bicyclo[2.2.1]hept-5-en-2-yl) piperidino-1-propanone (II) is obtained by a Diels-Alder cycloaddition reaction of cyclopentadiene and methyl vinyl ketone. A preferred method for preparing III, which affords a product with a high content of III-exo, is described in the parallel German patent application 10124450.9, the disclosure of which is incorporated herein by reference. The cycloaddition can be carried out in a solvent conventional for such reactions, such as diethyl ether, benzene, toluene or xylene or else without solvent. It is preferred to use no solvent. Cyclopentadiene and methyl vinyl ketone are normally employed in a molar ratio in the range from 3.0:1 to 0.5:1. They are preferably reacted equimolar or with cyclopentadiene in excess, with the excess preferably being 50 to 150 mol %.

The reaction is usually carried out at temperature in the range from 0 to 60° C., preferably in the range from 20 to 40° C.

Low-boiling constituents, usually unreacted precursors, are usually removed following the cycloaddition by distillation under reduced pressure, preferably under 1 to 150 mbar. The remaining mixture, which consists of about 20% exo- and about 80% endo-1-(bicyclo[2.2.1]hept-5-en-2-yl) ethanone, is reacted with an alkali metal $C_1$–$C_4$-alcoholate. The amount of alkali metal alcoholate is usually from 0.1 to 5% by weight, preferably from 0.2 to 2% by weight, based on the total weight of the mixture. Sodium methanolate is preferably used. The temperature necessary for isomerization of the ethanone III is usually in the range from 50 to 110° C., preferably in the range from 60 to 100° C. For this purpose, the mixture is often heated under reduced pressure to reflux, preferably under a pressure of from 1 to 100 mbar and in particular under a pressure of from 5 to 50 mbar. These conditions are usually applied for from 10 minutes to 5 hours, in particular 20 minutes to 3 hours and specifically 0.5 hours to 2 hours, and then fractional distillation of the resulting mixture is started, preferably distilling out the exo isomer of III. It is assumed that removal of the exo isomer from the equilibrium promotes isomerization of the endo ethanone to the exo form. The fractional distillation normally takes place through a column under reduced pressure, preferably in the range from 1 to 100 mbar, in particular from 1 to 50 and specifically from 1 to 20 mbar. The distillation temperature (distillate temperature) is preferably adjusted to from 50 to 100° C. and specifically to 50 to 80° C. In this way, exo-1-(bicyclo[2.2.1]-hept-5-en-2-yl)ethanone (III-exo) is obtained in a purity which is at least 96%. Redistillation of the distillate results in the exo ethanone III-exo with a purity of up to 100%.

The following example serves to illustrate the invention but is not to be understood as restrictive.

EXAMPLE

1. Preparation of the Starting Material 1.1 exo-1-(Bicyclo[2.2.1]hept-5-en-2-yl)ethanone (III-exo)

198.3 g of cyclopentadiene were rapidly added to 210.3 g of methyl vinyl ketone. After the addition was complete, the solution was stirred at room temperature for one hour and then unreacted precursor was removed by distillation at a temperature of 58° C. and a pressure of 20 mbar. The residue from evaporation, mainly consisting of a mixture of the exo and the endo form of 1-(bicyclo[2.2.1]hept-5-en-2-yl)ethanone (III) in the ratio of 1:4, was heated to reflux with 5 g of sodium methanolate under a pressure of from 10 to 20 mbar for one hour. The reaction mixture was then distilled through a column at a temperature of 75° C. and a pressure of 20 mbar. This resulted in 298.3 g (73% of theory) of exo-1-(bicyclo[2.2.1]hept-5-en-2-yl)ethanone (III-exo) in the form of a pale yellowish oil.

1.2    1-(Bicyclo[2.2.1]hept-5-en-2-yl)-3-piperidino-1-propanone (II)

68.1 g of exo-1-(bicyclo[2.2.1]hept-5-en-2-yl)ethanone (III-exo), 60.8 g of piperidine hydrochloride and 18 g of paraformaldehyde were heated to reflux in 140 ml of isopropanol for five hours. The solvent was removed in vacuo, and the residue was taken up in 100 ml of water. The solution was washed three times with 50 ml of diisopropyl ether each time and then adjusted to pH 10 with 50% strength sodium hydroxide solution. Three extractions each with 50 ml of diisopropyl ether were carried out, the three extracts were combined and the solvent was removed in a rotary evaporator. The residue from evaporation was distilled in a Kugelrohr at 75° C. under high vacuum at 0.001 mbar. The distillate obtained comprised 50.2 g (43% of theory) of a mixture of exo- and endo-1-(bicyclo[2.2.1]hept-5-en-2-yl)-3-piperidino-1-propanone (II) in the ratio 3.5:1 in the form of a colorless oil.

2. Preparation of Biperiden (Ia)

603.6 g (6.85 mol) of dioxane were added to 1 500 g of a 25% strength solution of phenylmagnesium chloride (375 g, 2.74 mol) in tetrahydrofuran while cooling to 0° C. in an ice bath, during which a white precipitate formed. After stirring while cooling in the ice bath for 30 min, 320 g (1.37 mol) of the 3.5:1 mixture of the exo and endo forms of 1-(bicyclo[2.2.1]hept-5-en-2-yl)-3-piperidino-1-propanone (II) were added while cooling in the ice bath. After the addition was complete, the ice bath was removed and the mixture was stirred at room temperature for one hour. The solution was subsequently added slowly to 1 500 ml of ice-cold water and then extracted three times with 500 ml of toluene each time. The organic phases were combined, dried over sodium sulfate and evaporated on a rotary evaporator. The residue from evaporation, 433.8 g of a mixture which consisted essentially of forms from Ia to Id of 1-(bicyclo [2.2.1]hept-5-en-2-yl)-1-phenyl-3-piperidino-1-propanone (I) in the ratio (GC) 10.4:3.4:3.0:1, was dissolved in 3 500 ml of hot 90% isopropanol, and 228 ml of a 6 molar solution of hydrogen chloride in isopropanol were added to the solution at 60° C. After the addition of acid, the mixture was stirred at 60° C. for one hour and then at the reflux temperature for 0.5 hours. After cooling to room temperature, the crystals which had separated out were removed and washed twice with 200 ml of isopropanol each time. The moist hydrochloride obtained in this way was stirred in 1 150 ml of diisopropyl ether and 350 ml of water while 135 ml of 5M sodium hydroxide solution were added. The mixture was heated to 55° C. and then, at this temperature, the aqueous phase was separated off and the diisopropyl ether solution was washed twice with 200 ml of water each time. 500 ml of solvent were removed from the washed diisopropyl ether solution by distillation under atmospheric pressure. The residue from distillation was allowed to cool while stirring. It was then cooled further to 20° C. and stirred at this temperature for one hour, and then the crystals which had separated out were removed, washed with 50 ml of diisopropyl ether and dried in vacuo at 50° C. 118 g of biperiden (Ia) were obtained as colorless crystals of melting point 112 to 114° C. (Ullmanns Enzyklopädie der techn. Chemie, 4th edition, volume 21, Verlag Chemie, 1982, page 627: 112–114° C.); which is 28% of theory.

3. Preparation of Biperiden Hydrochloride 6.7 g of biperiden (Ia) were dissolved in 75 ml of isopropanol by heating to the reflux temperature. The solution was filtered hot, and the filter was washed with 7 ml of isopropanol. 4.7 ml of 5 molar hydrochloric acid were added to the combined filtrates at 75° C. The mixture was then heated to reflux for 15 minutes. After cooling to room temperature, the precipitated solid was filtered off with suction, washed with 7 ml of isopropanol and dried in vacuo at 70° C. 7.3 g of biperiden hydrochloride were obtained in the form of colorless crystals of melting point 278 to 280° C. (Ullmanns Enzyklopädie der techn. Chemie, 4th edition, volume 21, Verlag Chemie, 1982, page 627: 278–280° C.); which is 98% of theory.

The invention claimed is:

1. A method for producing biperiden by reacting an exo/endo mixture of 1-(bicyclo-[2.2.1]hept-5-en-2-yl)-3-piperidino-1-propanone with an exo/endo ratio of at least 2.5:1 with a phenylmagnesium compound to give a biperiden-containing mixture of isomers of 1-(bicyclo-[2.2.1]hept-5-en-2-yl)-1-phenyl-3-piperidino-1-propanol, characterized in that the isolation of biperiden from the mixture of isomers comprises the following steps:
   a) reacting the mixture of isomers with HC1 in a mxture of water and a polar, water-miscible organic solvent, and isolation of the hydrochloride formed thereby,
   b) reacting the hydrochloride with heating in a mixture of water and at least one polar dialkyl ether of limited or zero miscibility with water and having 4 to 8 C atoms with a base,
   c) separating the two phases formed at elevated temperature,
   d) evaporating part of the ether from the organic phase and
   e) crystallizing of the biperiden by cooling.

2. The method of claim 1, characterized in that aqueous isopropanol is used as the solvent mixture in step a).

3. The method of claim 1, characterized in that the mxture of isomers is reacted in step a) with HC1 at a temperature in the range from 40 to 80° C.

4. The method of claim 1, characterized in that the hydrocholoride is isolated in step a) at a temperature in the range from 0° C. to 30° C.

5. The method of claim 1, characterized in that diisopropyl ether is used as the organic solvent in step b).

6. The method of claim 1, characterized in that an alkali metal or alkaline earth metal hydroxide or an alkali metal carbonate or a water-soluble organic base is used as the base in step b).

7. The method of claim 1, characterized in that the ether is evaporated in step d) until the weight/volume ratio of product to ether is in the range from 1:2 to 1:6.

8. The method of claim 1, characterized in that a phenylmagnesium halide, diphenylmagnesium or a phenylmagnesium alkoxide of the general formula IV

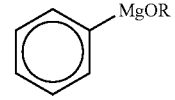

(IV)

where R is $C_1$–$C_4$-alkyl, $C_4$–$C_6$-cycloalkyl, $C_4$–$C_6$-cycloalkyl-$C_1$–$C_4$-alkyl, phenyl-$C_1$–$C_4$-alkyl, substituted phenyl- $C_1$–$C_4$-alkyl, heteroaryl, heteroaryl-$C_1$–$C_4$-alkyl or benzhydryl, is used as the phenylmagnesium compound.

9. The method of claim 8, characterized in that diphenylmagnesium or the phenylmagnesium alkoxide of the formula IV is employed as the phenylmagnesium compound.

10. The method of claim 9, characterized in that the phenylmagnesium alkoxide of the formula IV is prepared by reacting diphenylmagnesium with an alcohol of the general formula ROH where R has the meanings stated in claim 9.

11. The method of claim 9 characterized in that diphenylmagnesium is prepared by reacting a phenylmagnesium halide with dioxane, and the magnesium halide-dioxane complex which is formed at the same time is not removed.

* * * * *

UNITED STATES PATENT AND TRADEMARK OFFICE
CERTIFICATE OF CORRECTION

| | | |
|---|---|---|
| PATENT NO. | : 7,030,247 B2 | |
| APPLICATION NO. | : 10/477761 | |
| DATED | : April 18, 2006 | |
| INVENTOR(S) | : Peter Klein et al. | |

It is certified that error appears in the above-identified patent and that said Letters Patent is hereby corrected as shown below:

Column 12, line 41, is printed as "characterized in that the mxture" and should to corrected to read as "characterized in that the mixture".

Signed and Sealed this

Twenty-second Day of August, 2006

JON W. DUDAS
*Director of the United States Patent and Trademark Office*